United States Patent [19]
Verma et al.

[11] Patent Number: 5,994,053
[45] Date of Patent: Nov. 30, 1999

[54] PHRAGMOPLASTIN AND METHODS OF EXAMINING CELL PLATE DEVELOPMENT

[75] Inventors: Desh Pal S. Verma, Powell; Xiangju Gu, Columbus, both of Ohio

[73] Assignee: Ohio State University Research Foundation, Columbus, Ohio

[21] Appl. No.: 08/799,138

[22] Filed: Feb. 13, 1997

[51] Int. Cl.$^6$ .................................................. C12Q 1/00
[52] U.S. Cl. .............................. 435/4; 435/189; 435/518; 435/252.3
[58] Field of Search ........................... 435/4, 189, 252.3; 436/518

[56] References Cited

U.S. PATENT DOCUMENTS

| | | | |
|---|---|---|---|
| 5,491,084 | 2/1996 | Chalfie et al. | 435/189 |
| 5,514,600 | 5/1996 | Moss et al. | 436/518 |
| 5,541,109 | 7/1996 | Searfoss, III et al. | 435/252.3 |

OTHER PUBLICATIONS

Ricart, C.A.O. et al, J. Plant Physiol, vol. 146, pp. 645–651, 1995.
Dombrowski, J.E. et al, 1995, Plant Molecular Biol. vol. 28, pp. 1121–1126.
Gu, X et al, EMBO J, vol. 15 (4), Feb. 15, 1996, pp. 695–704.
BRL/Gibco Product & Reference Guide, 1997/1998, pp. 17–19, Top section.
EMBL, Apr. 1995 and Sep. 1995 Accession Nos. U25547, U36430, S63667, S63668.
Romero, L.C. et al, Proc. Natl. Acad. Sci, USA., vol. 90, Feb. 1993, pp. 1465–1469.
Borg, S. et al, Plant Mol. Biol., vol. 26, 1994, pp. 175–187.
Maddock, J. et al, J. of Bacteriol., Oct. 1997, vol. 179(20), pp. 6426–6431.
Cheong, N.E. et al, Plant Physiol., 1994, vol. 105, pp. 765–766.
Legendre, L. et al., Plant Physiol., 1993, pp. 233–240.
Cell, vol. 59, Howard S. Shpetner and Richard B. Vallee, "Identification of Dynamin, a Novel Mechanochemical Enzyme that Mediates Interactions between Microtubules", published Nov. 3, 1989 by Cell press, pp. 421–432.
"ATP–Sensitive Binding to Microtubules of Polypeptides Extracted from Isolated Phragmoplasts of Tobacco BY–2 Cells" by Yasuhara, et al., *Plant Cell Physiol.*, 33(5): 601–608 (1992).
"Dynamics of Phragmoplastin in Living Cells during Cell Plate Formation and Uncoupling of Cell Elongation from the Plane of Cell Division" by Gu, et al., *The Plant Cell*, vol. 9, Feb. 1997, pp. 157–169.
"The Effect of Benomyl and Carbendazim on Mitosis in Hyphae of *Botrytis cinerea* Pers. ex. Fr. and Roots of *Allim cepa L.*" by Richmond, et al., *Pesticide Biochamistry and Physiology*, vol. 5, No. 4, Aug. 1975, pp. 367–379.

*Primary Examiner*—James C. Housel
*Assistant Examiner*—Ginny Allen Portner
*Attorney, Agent, or Firm*—Calfee, Halter & Griswold LLP

[57] ABSTRACT

The present invention provides new tools and methods for identifying herbicides and potential herbicides which affect cell plate formation and development. A new protein, phragmoplastin, has been discovered which is associated with cell plate membrane vesicles during cytokinesis. By visualizing the phragmoplastin, one is able to examine the development of the cell plate particularly in response to herbicides or potential herbicides. One method of visualizing phragmoplastin employs immunocytochemical techniques with anti-phragmoplastin antibodies. Another method of visualizing phragmoplastin employs cells which are transformed with a DNA molecule which encodes a chimeric phragmoplastin protein comprised of phragmoplastin and a luminescent tag or protein, fused to the phragmoplastin protein. The phragmoplastin in such cells is visualized by examining the cells under conditions which cause the marker to become visible such as by fluorescent microscopy.

The present invention also relates to isolated DNA molecules which encode phragmoplastin, and cells transformed with DNA which encodes phragmoplastin, particularly DNA which encodes chimeric phragmoplastin proteins.

7 Claims, 7 Drawing Sheets

Fig. 1

```
   1 gcaccaagca ccaacaacgc tttagctctc tctcttctct ccataaccgc caccggcgat
  61 ctggcactaa cagatcgccg ctgctacatc tgaacccgat ccagccaaca gatctctcca
 121 attcaaatgg agaatctaat ctctttggtc aacaaaatcc agagagcttg caccgcctta
 181 ggtgaccacg gcgaaaacag tgcactcccc acactatggg actctctccc cgccatcgcc
 241 gtcgtcggag gccagagctc aggaaagtcc tccgtcttgg agagcgttgt cggcaaagat
 301 ttcttacctc gtggatcagg tattgttacg cgacgaccgc tcgtgttgca gcttcacaag
 361 attgaagagg aagcagaga gtacgcggag ttcctccacc tcccgaggaa gaggttcacc
 421 gattttgttg ctgtgaggaa ggagattcaa gacgaaactg atagagagac tggacgaacc
 481 aaacaaattt ctactgttcc cattcatctt agtatatact ctcccaatgt tgttaacttg
 541 acactcgttg atcttcctgg gcttacgaaa gtagctgttg agggtcaacc ggatagtatt
 601 gtgaaagaca ttgaggatat ggttcgctcc tacattgaga agccgaactg tataattttg
 661 gccatttcac cagccaatca agatcttgca acatctgatg caattaaaat ttcccgtgaa
 721 gtggaccgta ctggagatag gaccattgga gttttgacaa agattgatct tatggacaag
 781 ggtactgatg ctgttgatat attggaagga agagcatata ggttaaagtt tccctggatt
 841 ggtgttgtga atagatcaca acaagacata aacaagaatg ttgacatgat tgctgctagg
 901 cgtagagaac gtgagtactt caatagtacc cctgaatata acaccttgc gaacagaatg
 961 ggttccgagc atctggcgaa gatgctctca aagcatttgg agacagtaat caagtccaaa
1021 attcctggca ttcaatctct aattaacaaa acaattgctg aacttgaagc tgaactaact
1081 cgtttaggaa agcctgtagc agctgatgct gggggaaagt tgtatgcaat catggaaata
1141 tgccgctcat ttgatcaaat atttaaagac catcttgatg gcgtgcggcc tggaggtgat
1201 aaaatttata atgtctttga caatcagctc cccgctgctt taaaaaggtt gcagtttgat
1261 aagcagcttt caatggaaaa tataaggaaa cttattactg aagctgatgg gtatcagcct
1321 catcttatag ctccagaaca aggatatcgt gtctaattg aattcttctct aataactatt
1381 aggggccctg ctgaggcagc tgttgatgcg gttcactcgc tgttaaagga cttggttcac
1441 aaagctatca gtgagacttt ggacttgaag cagtatcctg gtctccgggt tgaggttggg
1501 gctgctgctg ttgattcact agaaagaatg agggatgaaa gcaaagagc aacactgcag
```

Fig. 1 (con't)

```
    1561 ctagttgata tggagtgtgg ctatctgact gttgatttct ttcggaagct
tcctcaagat
    1621 gttgataagg gtggcaatcc cacacattca atttttgata gatataatga
ttcatatcta
    1681 aggcgaattg gaaccacaat tttgtcatat gtcaatatgg tctgtgctac
actgcggaat
    1741 tcaattccca agtccatcgt ctattgtcaa gtgcgggagg caaaacgaag
tctacttgat
    1801 cacttttta ccgagctagg caaaatggag accaagcgtc tgtcatcgtt
attgaatgag
    1861 gatcctgcaa ttatggaacg acgtagtgcg ctcgcaaaga gactagagtt
ataccggagt
    1921 gcacaagctg aaatagatgc agttgcttgg tctaagtaga tatatgtatg
tcagatcacg
    1981 tttatacgag agccagcagt gtcattattc attgtttccc tatttccagt
tcattattca
    2041 tactcatttt ttgttgtcat cttatccact tgtattgtca tcttaaatag
atgagacgat
    2101 tctgaaaagg gaaaaaaatg attttttggg ttat
```

Fig. 2

```
   1 gaattcggca cgagcgtcgt aaaagcgagt atcccgttgg caatttggca
  51 tcacgtccct
  61 tttcaaacca agttccacag acaccaacaa cgctttagct ctctcttctc
     tccgtcaccg
 121 tcaccggcga tctacatctg aacccgatcc agccaataga tctcagaaat
     ccaaatggag
 181 aacctaatct ctttggtcaa caaaatccag agagcttgca ccgccttagg
     cgaccacgga
 241 gaaaacagtg cactccccac actatgggac tctcttcccg ccatcgccgt
     cgtcggaggc
 301 cagagctcag gaaagtcctc cgtcttggag agcgttgtcg gcaaagattt
     cttacctcgt
 361 ggatcaggca ttgttacgcg acgacctctc gtgttgcagc ttcacaagat
     tgacgaggga
 421 agcagggagt acgcagagtt cctccacctc ccgaggaaga ggttcaccga
     ttttgttgct
 481 gtgaggaagg agattcagga cgaaactgat agagagactg gacgaaccaa
     acaaatttcg
 541 agtgttccca ttcatcttag tatatactct cctaatgttg ttaacttgac
     gctcattgat
 601 cttcccggcc ttacgaaagt agctgtagag ggtcaaccgg atagtattgt
     gaaagacatt
 661 gaggatatgg ttcgctccta cattgagaag ccgaactgta aattttggc
     tatttcacca
 721 gccaatcaag atcttgcaac atccgatgca attaaaattt cccgtgaagt
     ggaccctact
 781 ggggatagga ccattggagt tttgacaaag attgatctta tggacaaggg
     tactgatgct
 841 gttgatatat tggaaggaag agcatatagg ttaaagtttc cctggattgg
     tgttgtgaat
 901 agatcacaac aagacataaa caagaatgtt gacatgattg ctgctaggcg
     tagagaacgt
 961 gagtacttta atagtacccc tgaatataaa caccttgcaa acagaatggg
     ttctgaacat
1021 ctggcgaaga tgctctcaaa gcatttggag acagtaatca agtccaaat
     tcctggcatt
1081 caatccctaa ttaacaaaac aattgccgaa cttgaagctg aactaactcg
     tttaggaaaa
1141 cctgttgcag ctgatgctgg gggaaagttg tatgctatca tggaaatatg
     ccgctcattt
1201 gatcaaatat ttaaagacca tcttgatggc gtgcggcctg gaggtgataa
     aatttataat
1261 gtctttgaca atcagctccc tgctgcttta aaaaggttgc agtttgataa
     gcagctttca
1321 atggaaaata taaggaaact tattacagaa gctgatgggt atcagcctca
     tctaatagct
1381 ccagaacaag gataccgtcg cctaattgaa tcttctctaa taactattag
     gggccctgct
1441 gagtcagctg ttgatgcggt tcactccctg ttaaaggact tggttcacaa
     agctatgagt
1501 gagactttgg acttgaagca gtatcctggt ctccggggttg aggttggggc
     tgcatctgtt
```

Fig. 2 (con't)

```
    1561 gattcactcg aaagaatgag ggatgaaagc aaagagcaa cactgcagct
agttgatatg
    1621 gagtgtggct atctgactgt tgatttcttt cggaagcttc ctcaagatgt
tgataagggt
    1681 ggcaatccca cacattcaat ttgtgataga tataatgatt catatctaag
gcgaattgga
    1741 accacaattt tgtcatatgt caatatggtc tgtgctactc tgcggcattc
aattcccaag
    1801 tccatcgtct attgtcaagt gcgggaggca aaacgaagtc tacttgatca
cttttttacc
    1861 gagctaggca aaatggagat caagcgtctg tcctcgttac tgaatgagga
tcctgcaatt
    1921 atggaacgac gtagtgcgct cgcaaagaga ctagagttat accggagtgc
acaagctgaa
    1981 atagatgcag ttgcttggtc taagtagaga tatgtatgtc aaatcacgtt
tatacgagag
    2041 ccagcagtgt cattatcatt gttcactatt ttcttattca tactcatttt
tcattgtcat
    2101 cttattctgt tgcatttcct cttgaataga tgagacgatt ctgaaaaagg
gaaaaaatga
    2161 tttttgggt tatatataat tgagtgtccc tatatctttc atttttagt
c
```

Fig. 3

MENLISLVNKIQRACTALGDHGENSALPTLWDSLPAIAVVGGQS

SGKSSVLESVVGKDFLPRGSGIVTRRPLVLQLHKIEEGSREYAEFLHLPRKRFTDFVA

VRKEIQDETDRETGRTKQISTVPIHLSIYSPNVVNLTLVDLPGLTKVAVEGQPDSIVK

DIEDMVRSYIEKPNCIILAISPANQDLATSDAIKISREVDPTGDRTIGVLTKIDLMDK

GTDAVDILEGRAYRLKFPWIGVVNRSQQDINKNVDMIAARRREREYFNSTPEYKHLAN

RMGSEHLAKMLSKHLETVIKSKIPGIQSLINKTIAELEAELTRLGKPVAADAGGKLYA

IMEICRSFDQIFKDHLDGVRPGGDKIYNVFDNQLPAALKRLQFDKQLSMENIRKLITE

ADGYQPHLIAPEQGYRRLIESSLITIRGPAEAAVDAVHSLLKDLVHKAISETLDLKQY

PGLRVEVGAAAVDSLERMRDESKRATLQLVDMECGYLTVDFFRKLPQDVDKGGNPTHS

IFDRYNDSYLRRIGTTILSYVNMVCATLRNSIPKSIVYCQVREAKRSLLDHFFTELGK

METKRLSSLLNEDPAIMERRSALAKRLELYRSAQAEIDAVAWSK"

Fig. 4

MENLISLVNKIQRACTALGDHGENSALPTLWDSLPAIAVVGGQS
SGKSSVLESVVGKDFLPRGSGIVTRRPLVLQLHKIDEGSREYAEFLHLPRKRFTDFVA
VRKEIQDETDRETGRTKQISSVPIHLSIYSPNVVNLTLIDLPGLTKVAVEGQPDSIVK
DIEDMVRSYIEKPNCIILAISPANQDLATSDAIKISREVDPTGDRTIGVLTKIDLMDK
GTDAVDILEGRAYRLKFPWIGVVNRSQQDINKNVDMIAARRREREYFNSTPEYKHLAN
RMGSEHLAKMLSKHLETVIKSKIPGIQSLINKTIAELEAELTRLGKPVAADAGGKLYA
IMEICRSFDQIFKDHLDGVRPGGDKIYNVFDNQLPAALKRLQFDKQLSMENIRKLITE
ADGYQPHLIAPEQGYRRLIESSLITIRGPAESAVDAVHSLLKDLVHKAMSETLDLKQY
PGLRVEVGAASVDSLERMRDESKRATLQLVDMECGYLTVDFFRKLPQDVDKGGNPTHS
ICDRYNDSYLRRIGTTILSYVNMVCATLRHSIPKSIVYCQVREAKRSLLDHFFTELGK
MEIKRLSSLLNEDPAIMERRSALAKRLELYRSAQAEIDAVAWSK"

PB1121-EGP

```
                              SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
           (A) LENGTH: 23 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (ix) FEATURE:
           (A) NAME/KEY: modified_base
           (B) LOCATION: 15

(ix) FEATURE:
           (A) NAME/KEY: modified_base
           (B) LOCATION: 21

(xi) SEQUENCE DESCRIPTION: SEQ ID NO:1:

CCNMGMGGWW STGGNATYGT NAC                                                    23

(2) INFORMATION FOR SEQ ID NO:2:

(i) SEQUENCE CHARACTERISTICS:
```

(A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: modified_base
        (B) LOCATION: 7

(ix) FEATURE:
        (A) NAME/KEY: modified_base
        (B) LOCATION: 13

(ix) FEATURE:
        (A) NAME/KEY: modified_base
        (B) LOCATION: 19

(xi) SEQUENCE DESCRIPTION: SEQ ID NO:2:

TTTKGTNAWR ACNCCDATNG T                                        21

(2) INFORMATION FOR SEQ ID NO:3:

(i) SEQUENCE CHARACTERISTICS:
        (A) LENGTH: 2134 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 127..1956

(xi) SEQUENCE DESCRIPTION: SEQ ID NO:3:

GCACCAAGCA CCAACAACGC TTTAGCTCTC TCTCTTCTCT CCATAACCGC CACCGGCGAT      60

CTGGCACTAA CAGATCGCCG CTGCTACATC TGAACCCGAT CCAGCCAACA GATCTCTCCA     120

ATTCAA ATG GAG AAT CTA ATC TCT TTG GTC AAC AAA ATC CAG AGA GCT        168
       Met Glu Asn Leu Ile Ser Leu Val Asn Lys Ile Gln Arg Ala
        1               5                  10

TGC ACC GCC TTA GGT GAC CAC GGC GAA AAC AGT GCA CTC CCC ACA CTA       216
Cys Thr Ala Leu Gly Asp His Gly Glu Asn Ser Ala Leu Pro Thr Leu
 15              20                  25                  30

TGG GAC TCT CTC CCC GCC ATC GCC GTC GTC GGA GGC CAG AGC TCA GGA       264
Trp Asp Ser Leu Pro Ala Ile Ala Val Val Gly Gly Gln Ser Ser Gly
             35                  40                  45

AAG TCC TCC GTC TTG GAG AGC GTT GTC GGC AAA GAT TTC TTA CCT CGT       312
Lys Ser Ser Val Leu Glu Ser Val Val Gly Lys Asp Phe Leu Pro Arg
         50                  55                  60

GGA TCA GGT ATT GTT ACG CGA CGA CCG CTC GTG TTG CAG CTT CAC AAG       360
Gly Ser Gly Ile Val Thr Arg Arg Pro Leu Val Leu Gln Leu His Lys
     65                  70                  75

ATT GAA GAG GGA AGC AGA GAG TAC GCG GAG TTC CTC CAC CTC CCG AGG       408
Ile Glu Glu Gly Ser Arg Glu Tyr Ala Glu Phe Leu His Leu Pro Arg
 80                  85                  90

AAG AGG TTC ACC GAT TTT GTT GCT GTG AGG AAG GAG ATT CAA GAC GAA       456
Lys Arg Phe Thr Asp Phe Val Ala Val Arg Lys Glu Ile Gln Asp Glu
         95                 100                 105                 110

ACT GAT AGA GAG ACT GGA CGA ACC AAA CAA ATT TCT ACT GTT CCC ATT       504
Thr Asp Arg Glu Thr Gly Arg Thr Lys Gln Ile Ser Thr Val Pro Ile
                 115                 120                 125

-continued

| | | | | | | | | | | | | | | | |
|---|---|---|---|---|---|---|---|---|---|---|---|---|---|---|---|
| CAT | CTT | AGT | ATA | TAC | TCT | CCC | AAT | GTT | GTT | AAC | TTG | ACA | CTC | GTT | GAT | 552 |
| His | Leu | Ser | Ile | Tyr | Ser | Pro | Asn | Val | Val | Asn | Leu | Thr | Leu | Val | Asp | |
| | | | 130 | | | | | 135 | | | | | 140 | | | |

| CTT | CCT | GGG | CTT | ACG | AAA | GTA | GCT | GTT | GAG | GGT | CAA | CCG | GAT | AGT | ATT | 600 |
| Leu | Pro | Gly | Leu | Thr | Lys | Val | Ala | Val | Glu | Gly | Gln | Pro | Asp | Ser | Ile | |
| | | 145 | | | | | 150 | | | | | 155 | | | | |

| GTG | AAA | GAC | ATT | GAG | GAT | ATG | GTT | CGC | TCC | TAC | ATT | GAG | AAG | CCG | AAC | 648 |
| Val | Lys | Asp | Ile | Glu | Asp | Met | Val | Arg | Ser | Tyr | Ile | Glu | Lys | Pro | Asn | |
| | 160 | | | | | 165 | | | | | 170 | | | | | |

| TGT | ATA | ATT | TTG | GCC | ATT | TCA | CCA | GCC | AAT | CAA | GAT | CTT | GCA | ACA | TCT | 696 |
| Cys | Ile | Ile | Leu | Ala | Ile | Ser | Pro | Ala | Asn | Gln | Asp | Leu | Ala | Thr | Ser | |
| 175 | | | | | 180 | | | | | 185 | | | | | 190 | |

| GAT | GCA | ATT | AAA | ATT | TCC | CGT | GAA | GTG | GAC | CCT | ACT | GGA | GAT | AGG | ACC | 744 |
| Asp | Ala | Ile | Lys | Ile | Ser | Arg | Glu | Val | Asp | Pro | Thr | Gly | Asp | Arg | Thr | |
| | | | | 195 | | | | | 200 | | | | | 205 | | |

| ATT | GGA | GTT | TTG | ACA | AAG | ATT | GAT | CTT | ATG | GAC | AAG | GGT | ACT | GAT | GCT | 792 |
| Ile | Gly | Val | Leu | Thr | Lys | Ile | Asp | Leu | Met | Asp | Lys | Gly | Thr | Asp | Ala | |
| | | | 210 | | | | | 215 | | | | | 220 | | | |

| GTT | GAT | ATA | TTG | GAA | GGA | AGA | GCA | TAT | AGG | TTA | AAG | TTT | CCC | TGG | ATT | 840 |
| Val | Asp | Ile | Leu | Glu | Gly | Arg | Ala | Tyr | Arg | Leu | Lys | Phe | Pro | Trp | Ile | |
| | | 225 | | | | | 230 | | | | | 235 | | | | |

| GGT | GTT | GTG | AAT | AGA | TCA | CAA | CAA | GAC | ATA | AAC | AAG | AAT | GTT | GAC | ATG | 888 |
| Gly | Val | Val | Asn | Arg | Ser | Gln | Gln | Asp | Ile | Asn | Lys | Asn | Val | Asp | Met | |
| | 240 | | | | | 245 | | | | | 250 | | | | | |

| ATT | GCT | GCT | AGG | CGT | AGA | GAA | CGT | GAG | TAC | TTC | AAT | AGT | ACC | CCT | GAA | 936 |
| Ile | Ala | Ala | Arg | Arg | Arg | Glu | Arg | Glu | Tyr | Phe | Asn | Ser | Thr | Pro | Glu | |
| 255 | | | | | 260 | | | | | 265 | | | | | 270 | |

| TAT | AAA | CAC | CTT | GCG | AAC | AGA | ATG | GGT | TCC | GAG | CAT | CTG | GCG | AAG | ATG | 984 |
| Tyr | Lys | His | Leu | Ala | Asn | Arg | Met | Gly | Ser | Glu | His | Leu | Ala | Lys | Met | |
| | | | | 275 | | | | | 280 | | | | | 285 | | |

| CTC | TCA | AAG | CAT | TTG | GAG | ACA | GTA | ATC | AAG | TCC | AAA | ATT | CCT | GGC | ATT | 1032 |
| Leu | Ser | Lys | His | Leu | Glu | Thr | Val | Ile | Lys | Ser | Lys | Ile | Pro | Gly | Ile | |
| | | | 290 | | | | | 295 | | | | | 300 | | | |

| CAA | TCT | CTA | ATT | AAC | AAA | ACA | ATT | GCT | GAA | CTT | GAA | GCT | GAA | CTA | ACT | 1080 |
| Gln | Ser | Leu | Ile | Asn | Lys | Thr | Ile | Ala | Glu | Leu | Glu | Ala | Glu | Leu | Thr | |
| | | | 305 | | | | | 310 | | | | | 315 | | | |

| CGT | TTA | GGA | AAG | CCT | GTA | CGA | GCT | GAT | GCT | GGG | GGA | AAG | TTG | TAT | GCA | 1128 |
| Arg | Leu | Gly | Lys | Pro | Val | Arg | Ala | Asp | Ala | Gly | Gly | Lys | Leu | Tyr | Ala | |
| | 320 | | | | | 325 | | | | | 330 | | | | | |

| ATC | ATG | GAA | ATA | TGC | CGC | TCA | TTT | GAT | CAA | ATA | TTT | AAA | GAC | CAT | CTT | 1176 |
| Ile | Met | Glu | Ile | Cys | Arg | Ser | Phe | Asp | Gln | Ile | Phe | Lys | Asp | His | Leu | |
| 335 | | | | | 340 | | | | | 345 | | | | | 350 | |

| GAT | GGC | GTG | CGG | CCT | GGA | GGT | GAT | AAA | ATT | TAT | AAT | GTC | TTT | GAC | AAT | 1224 |
| Asp | Gly | Val | Arg | Pro | Gly | Gly | Asp | Lys | Ile | Tyr | Asn | Val | Phe | Asp | Asn | |
| | | | | 355 | | | | | 360 | | | | | 365 | | |

| CAG | CTC | CCC | GCT | GCT | TTA | AAA | AGG | TTG | CAG | TTT | GAT | AAG | CAG | CTT | TCA | 1272 |
| Gln | Leu | Pro | Ala | Ala | Leu | Lys | Arg | Leu | Gln | Phe | Asp | Lys | Gln | Leu | Ser | |
| | | | 370 | | | | | 375 | | | | | 380 | | | |

| ATG | GAA | AAT | ATA | AGG | AAA | CTT | ATT | ACT | GAA | GCT | GAT | GGG | TAT | CAG | CCT | 1320 |
| Met | Glu | Asn | Ile | Arg | Lys | Leu | Ile | Thr | Glu | Ala | Asp | Gly | Tyr | Gln | Pro | |
| | | 385 | | | | | 390 | | | | | 395 | | | | |

| CAT | CTT | ATA | GCT | CCA | GAA | CAA | GGA | TAT | CGT | CGT | CTA | ATT | GAA | TCT | TCT | 1368 |
| His | Leu | Ile | Ala | Pro | Glu | Gln | Gly | Tyr | Arg | Arg | Leu | Ile | Glu | Ser | Ser | |
| | 400 | | | | | 405 | | | | | 410 | | | | | |

| CTA | ATA | ACT | ATT | AGG | GGC | CCT | GCT | GAG | GCA | GCT | GTT | GAT | GCG | GTT | CAC | 1416 |
| Leu | Ile | Thr | Ile | Arg | Gly | Pro | Ala | Glu | Ala | Ala | Val | Asp | Ala | Val | His | |
| 415 | | | | | 420 | | | | | 425 | | | | | 430 | |

| TCG | CTG | TTA | AAG | GAC | TTG | GTT | CAC | AAA | GCT | ATC | AGT | GAG | ACT | TTG | GAC | 1464 |
| Ser | Leu | Leu | Lys | Asp | Leu | Val | His | Lys | Ala | Ile | Ser | Glu | Thr | Leu | Asp | |
| | | | 435 | | | | | 440 | | | | | 445 | | | |

-continued

```
TTG AAG CAG TAT CCT GGT CTC CGG GTT GAG GTT GGG GCT GCT GCT GTT    1512
Leu Lys Gln Tyr Pro Gly Leu Arg Val Glu Val Gly Ala Ala Ala Val
            450                 455                 460

GAT TCA CTA GAA AGA ATG AGG GAT GAA AGC AAA AGA GCA ACA CTG CAG    1560
Asp Ser Leu Glu Arg Met Arg Asp Glu Ser Lys Arg Ala Thr Leu Gln
465                 470                 475

CTA GTT GAT ATG GAG TGT GGC TAT CTG ACT GTT GAT TTC TTT CGG AAG    1608
Leu Val Asp Met Glu Cys Gly Tyr Leu Thr Val Asp Phe Phe Arg Lys
        480                 485                 490

CTT CCT CAA GAT GTT GAT AAG GGT GGC AAT CCC ACA CAT TCA ATT TTT    1656
Leu Pro Gln Asp Val Asp Lys Gly Gly Asn Pro Thr His Ser Ile Phe
495                 500                 505                 510

GAT AGA TAT AAT GAT TCA TAT CTA AGG CGA ATT GGA ACC ACA ATT TTG    1704
Asp Arg Tyr Asn Asp Ser Tyr Leu Arg Arg Ile Gly Thr Thr Ile Leu
                515                 520                 525

TCA TAT GTC AAT ATG GTC TGT GCT ACA CTG CGG AAT TCA ATT CCC AAG    1752
Ser Tyr Val Asn Met Val Cys Ala Thr Leu Arg Asn Ser Ile Pro Lys
            530                 535                 540

TCC ATC GTC TAT TGT CAA GTG CGG GAG GCA AAA CGA AGT CTA CTT GAT    1800
Ser Ile Val Tyr Cys Gln Val Arg Glu Ala Lys Arg Ser Leu Leu Asp
        545                 550                 555

CAC TTT TTT ACC GAG CTA GGC AAA ATG GAG ACC AAG CGT CTG TCA TCG    1848
His Phe Phe Thr Glu Leu Gly Lys Met Glu Thr Lys Arg Leu Ser Ser
560                 565                 570

TTA TTG AAT GAG GAT CCT GCA ATT ATG GAA CGA CGT AGT GCG CTC GCA    1896
Leu Leu Asn Glu Asp Pro Ala Ile Met Glu Arg Arg Ser Ala Leu Ala
575                 580                 585                 590

AAG AGA CTA GAG TTA TAC CGG AGT GCA CAA GCT GAA ATA GAT GCA GTT    1944
Lys Arg Leu Glu Leu Tyr Arg Ser Ala Gln Ala Glu Ile Asp Ala Val
                595                 600                 605

GCT TGG TCT AAG TAGATATATG TATGTCAGAT CACGTTTATA CGAGAGCCAG        1996
Ala Trp Ser Lys
            610

CAGTGTCATT ATTCATTGTT TCCCTATTTC CAGTTCATTA TTCATACTCA TTTTTTGTTG  2056

TCATCTTATC CACTTGTATT GTCATCTTAA ATAGATGAGA CGATTCTGAA AAGGGAAAAA  2116

AATGATTTTT TGGGTTAT                                                 2134

(2) INFORMATION FOR SEQ ID NO:4:

(i) SEQUENCE CHARACTERISTICS:
        (A) LENGTH: 610 amino acids
        (B) TYPE: amino acid
        (D) TOPOLOGY: linear (ii) MOLECULE TYPE: protein (xi) SEQUENCE DESCRIPTION: SEQ ID NO:4:

Met Glu Asn Leu Ile Ser Leu Val Asn Lys Ile Gln Arg Ala Cys Thr
1               5                   10                  15

Ala Leu Gly Asp His Gly Glu Asn Ser Ala Leu Pro Thr Leu Trp Asp
            20                  25                  30

Ser Leu Pro Ala Ile Ala Val Val Gly Gly Gln Ser Ser Gly Lys Ser
        35                  40                  45

Ser Val Leu Glu Ser Val Val Gly Lys Asp Phe Leu Pro Arg Gly Ser
    50                  55                  60

Gly Ile Val Thr Arg Arg Pro Leu Val Leu Gln Leu His Lys Ile Glu
65                  70                  75                  80

Glu Gly Ser Arg Glu Tyr Ala Glu Phe Leu His Leu Pro Arg Lys Arg
                85                  90                  95
```

```
Phe Thr Asp Phe Val Ala Val Arg Lys Glu Ile Gln Asp Glu Thr Asp
            100                 105                 110

Arg Glu Thr Gly Arg Thr Lys Gln Ile Ser Thr Val Pro Ile His Leu
            115                 120                 125

Ser Ile Tyr Ser Pro Asn Val Asn Leu Thr Leu Val Asp Leu Pro
            130                 135                 140

Gly Leu Thr Lys Val Ala Val Glu Gly Gln Pro Asp Ser Ile Val Lys
145                 150                 155                 160

Asp Ile Glu Asp Met Val Arg Ser Tyr Ile Glu Lys Pro Asn Cys Ile
                    165                 170                 175

Ile Leu Ala Ile Ser Pro Ala Asn Gln Asp Leu Ala Thr Ser Asp Ala
                180                 185                 190

Ile Lys Ile Ser Arg Glu Val Asp Pro Thr Gly Asp Arg Thr Ile Gly
            195                 200                 205

Val Leu Thr Lys Ile Asp Leu Met Asp Lys Gly Thr Asp Ala Val Asp
210                 215                 220

Ile Leu Glu Gly Arg Ala Tyr Arg Leu Lys Phe Pro Trp Ile Gly Val
225                 230                 235                 240

Val Asn Arg Ser Gln Gln Asp Ile Asn Lys Asn Val Asp Met Ile Ala
                245                 250                 255

Ala Arg Arg Arg Glu Arg Glu Tyr Phe Asn Ser Thr Pro Glu Tyr Lys
            260                 265                 270

His Leu Ala Asn Arg Met Gly Ser Glu His Leu Ala Lys Met Leu Ser
            275                 280                 285

Lys His Leu Glu Thr Val Ile Lys Ser Lys Ile Pro Gly Ile Gln Ser
290                 295                 300

Leu Ile Asn Lys Thr Ile Ala Glu Leu Glu Ala Glu Leu Thr Arg Leu
305                 310                 315                 320

Gly Lys Pro Val Arg Ala Asp Ala Gly Gly Lys Leu Tyr Ala Ile Met
                325                 330                 335

Glu Ile Cys Arg Ser Phe Asp Gln Ile Phe Lys Asp His Leu Asp Gly
            340                 345                 350

Val Arg Pro Gly Gly Asp Lys Ile Tyr Asn Val Phe Asp Asn Gln Leu
            355                 360                 365

Pro Ala Ala Leu Lys Arg Leu Gln Phe Asp Lys Gln Leu Ser Met Glu
370                 375                 380

Asn Ile Arg Lys Leu Ile Thr Glu Ala Asp Gly Tyr Gln Pro His Leu
385                 390                 395                 400

Ile Ala Pro Glu Gln Gly Tyr Arg Arg Leu Ile Glu Ser Ser Leu Ile
                405                 410                 415

Thr Ile Arg Gly Pro Ala Glu Ala Val Asp Ala Val His Ser Leu
            420                 425                 430

Leu Lys Asp Leu Val His Lys Ala Ile Ser Glu Thr Leu Asp Leu Lys
            435                 440                 445

Gln Tyr Pro Gly Leu Arg Val Glu Val Gly Ala Ala Val Asp Ser
    450                 455                 460

Leu Glu Arg Met Arg Asp Glu Ser Lys Arg Ala Thr Leu Gln Leu Val
465                 470                 475                 480

Asp Met Glu Cys Gly Tyr Leu Thr Val Asp Phe Phe Arg Lys Leu Pro
                485                 490                 495

Gln Asp Val Asp Lys Gly Gly Asn Pro Thr His Ser Ile Phe Asp Arg
            500                 505                 510

Tyr Asn Asp Ser Tyr Leu Arg Arg Ile Gly Thr Thr Ile Leu Ser Tyr
            515                 520                 525
```

```
Val Asn Met Val Cys Ala Thr Leu Arg Asn Ser Ile Pro Lys Ser Ile
    530                 535                 540

Val Tyr Cys Gln Val Arg Glu Ala Lys Arg Ser Leu Leu Asp His Phe
545                 550                 555                 560

Phe Thr Glu Leu Gly Lys Met Glu Thr Lys Arg Leu Ser Ser Leu Leu
                565                 570                 575

Asn Glu Asp Pro Ala Ile Met Glu Arg Arg Ser Ala Leu Ala Lys Arg
                580                 585                 590

Leu Glu Leu Tyr Arg Ser Ala Gln Ala Glu Ile Asp Ala Val Ala Trp
            595                 600                 605

Ser Lys
    610

(2) INFORMATION FOR SEQ ID NO:5:

(i) SEQUENCE CHARACTERISTICS:
        (A) LENGTH: 2211 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 175..2004

(xi) SEQUENCE DESCRIPTION: SEQ ID NO:5:

GAATTCGGCA CGAGCGTCGT AAAAGCGAGT ATCCCGTTGG CAATTTGGCA TCACGTCCCT      60

TTTCAAACCA AGTTCCACAG ACACCAACAA CGCTTTAGCT CTCTCTTCTC TCCGTCACCG     120

TCACCGGCGA TCTACATCTG AACCCGATCC AGCCAATAGA TCTCAGAAAT CCAA ATG      177
                                                               Met
                                                                 1

GAG AAC CTA ATC TCT TTG GTC AAC AAA ATC CAG AGA GCT TGC ACC GCC      225
Glu Asn Leu Ile Ser Leu Val Asn Lys Ile Gln Arg Ala Cys Thr Ala
            5                  10                  15

TTA GGC GAC CAC GGA GAA AAC AGT GCA CTC CCC ACA CTA TGG GAC TCT      273
Leu Gly Asp His Gly Glu Asn Ser Ala Leu Pro Thr Leu Trp Asp Ser
        20                  25                  30

CTT CCC GCC ATC GCC GTC GTC GGA GGC CAG AGC TCA GGA AAG TCC TCC      321
Leu Pro Ala Ile Ala Val Val Gly Gly Gln Ser Ser Gly Lys Ser Ser
    35                  40                  45

GTC TTG GAG AGC GTT GTC GGC AAA GAT TTC TTA CCT CGT GGA TCA GGC      369
Val Leu Glu Ser Val Val Gly Lys Asp Phe Leu Pro Arg Gly Ser Gly
 50                  55                  60                  65

ATT GTT ACG CGA CGA CCT CTC GTG TTG CAG CTT CAC AAG ATT GAC GAG      417
Ile Val Thr Arg Arg Pro Leu Val Leu Gln Leu His Lys Ile Asp Glu
                 70                  75                  80

GGA AGC AGG GAG TAC GCA GAG TTC CTC CAC CTC CCG AGG AAG AGG TTC      465
Gly Ser Arg Glu Tyr Ala Glu Phe Leu His Leu Pro Arg Lys Arg Phe
             85                  90                  95

ACC GAT TTT GTT GCT GTG AGG AAG GAG ATT CAG GAC GAA ACT GAT AGA      513
Thr Asp Phe Val Ala Val Arg Lys Glu Ile Gln Asp Glu Thr Asp Arg
            100                 105                 110

GAG ACT GGA CGA ACC AAA CAA ATT TCG AGT GTT CCC ATT CAT CTT AGT      561
Glu Thr Gly Arg Thr Lys Gln Ile Ser Ser Val Pro Ile His Leu Ser
        115                 120                 125

ATA TAC TCT CCT AAT GTT GTT AAC TTG ACG CTC ATT GAT CTT CCC GGC      609
Ile Tyr Ser Pro Asn Val Val Asn Leu Thr Leu Ile Asp Leu Pro Gly
130                 135                 140                 145
```

| | | |
|---|---|---|
| CTT ACG AAA GTA GCT GTA GAG GGT CAA CCG GAT AGT ATT GTG AAA GAC<br>Leu Thr Lys Val Ala Val Glu Gly Gln Pro Asp Ser Ile Val Lys Asp<br>              150                        155                     160 | | 657 |
| ATT GAG GAT ATG GTT CGC TCC TAC ATT GAG AAG CCG AAC TGT ATA ATT<br>Ile Glu Asp Met Val Arg Ser Tyr Ile Glu Lys Pro Asn Cys Ile Ile<br>              165                       170                     175 | | 705 |
| TTG GCT ATT TCA CCA GCC AAT CAA GAT CTT GCA ACA TCC GAT GCA ATT<br>Leu Ala Ile Ser Pro Ala Asn Gln Asp Leu Ala Thr Ser Asp Ala Ile<br>        180                       185                     190 | | 753 |
| AAA ATT TCC CGT GAA GTG GAC CCT ACT GGG GAT AGG ACC ATT GGA GTT<br>Lys Ile Ser Arg Glu Val Asp Pro Thr Gly Asp Arg Thr Ile Gly Val<br>195                     200                     205 | | 801 |
| TTG ACA AAG ATT GAT CTT ATG GAC AAG GGT ACT GAT GCT GTT GAT ATA<br>Leu Thr Lys Ile Asp Leu Met Asp Lys Gly Thr Asp Ala Val Asp Ile<br>210                     215                     220                     225 | | 849 |
| TTG GAA GGA AGA GCA TAT AGG TTA AAG TTT CCC TGG ATT GGT GTT GTG<br>Leu Glu Gly Arg Ala Tyr Arg Leu Lys Phe Pro Trp Ile Gly Val Val<br>                     230                     235                     240 | | 897 |
| AAT AGA TCA CAA CAA GAC ATA AAC AAG AAT GTT GAC ATG ATT GCT GCT<br>Asn Arg Ser Gln Gln Asp Ile Asn Lys Asn Val Asp Met Ile Ala Ala<br>            245                     250                     255 | | 945 |
| AGG CGT AGA GAA CGT GAG TAC TTT AAT AGT ACC CCT GAA TAT AAA CAC<br>Arg Arg Arg Glu Arg Glu Tyr Phe Asn Ser Thr Pro Glu Tyr Lys His<br>        260                     265                     270 | | 993 |
| CTT GCA AAC AGA ATG GGT TCT GAA CAT CTG GCG AAG ATG CTC TCA AAG<br>Leu Ala Asn Arg Met Gly Ser Glu His Leu Ala Lys Met Leu Ser Lys<br>275                     280                     285 | | 1041 |
| CAT TTG GAG ACA GTA ATC AAG TCC AAA ATT CCT GGC ATT CAA TCC CTA<br>His Leu Glu Thr Val Ile Lys Ser Lys Ile Pro Gly Ile Gln Ser Leu<br>290                     295                     300                     305 | | 1089 |
| ATT AAC AAA ACA ATT GCC GAA CTT GAA GCT GAA CTA ACT CGT TTA GGA<br>Ile Asn Lys Thr Ile Ala Glu Leu Glu Ala Glu Leu Thr Arg Leu Gly<br>                     310                     315                     320 | | 1137 |
| AAA CCT GTT GCA GCT GAT GCT GGG GGA AAG TTG TAT GCT ATC ATG GAA<br>Lys Pro Val Ala Ala Asp Ala Gly Gly Lys Leu Tyr Ala Ile Met Glu<br>            325                     330                     335 | | 1185 |
| ATA TGC CGC TCA TTT GAT CAA ATA TTT AAA GAC CAT CTT GAT GGC GTG<br>Ile Cys Arg Ser Phe Asp Gln Ile Phe Lys Asp His Leu Asp Gly Val<br>                340                     345                     350 | | 1233 |
| CGG CCT GGA GGT GAT AAA ATT TAT AAT GTC TTT GAC AAT CAG CTC CCT<br>Arg Pro Gly Gly Asp Lys Ile Tyr Asn Val Phe Asp Asn Gln Leu Pro<br>355                     360                     365 | | 1281 |
| GCT GCT TTA AAA AGG TTG CAG TTT GAT AAG CAG CTT TCA ATG GAA AAT<br>Ala Ala Leu Lys Arg Leu Gln Phe Asp Lys Gln Leu Ser Met Glu Asn<br>370                     375                     380                     385 | | 1329 |
| ATA AGG AAA CTT ATT ACA GAA GCT GAT GGG TAT CAG CCT CAT CTA ATA<br>Ile Arg Lys Leu Ile Thr Glu Ala Asp Gly Tyr Gln Pro His Leu Ile<br>              390                     395                     400 | | 1377 |
| GCT CCA GAA CAA GGA TAC CGT CGC CTA ATT GAA TCT TCT CTA ATA ACT<br>Ala Pro Glu Gln Gly Tyr Arg Arg Leu Ile Glu Ser Ser Leu Ile Thr<br>            405                     410                     415 | | 1425 |
| ATT AGG GGC CCT GCT GAG TCA GCT GTT GAT GCG GTT CAC TCC CTG TTA<br>Ile Arg Gly Pro Ala Glu Ser Ala Val Asp Ala Val His Ser Leu Leu<br>              420                     425                     430 | | 1473 |
| AAG GAC TTG GTT CAC AAA GCT ATG AGT GAG ACT TTG GAC TTG AAG CAG<br>Lys Asp Leu Val His Lys Ala Met Ser Glu Thr Leu Asp Leu Lys Gln<br>435                     440                     445 | | 1521 |
| TAT CCT GGT CTC CGG GTT GAG GTT GGG GCT GCA TCT GTT GAT TCA CTC<br>Tyr Pro Gly Leu Arg Val Glu Val Gly Ala Ala Ser Val Asp Ser Leu<br>450                     455                     460                     465 | | 1569 |

```
GAA AGA ATG AGG GAT GAA AGC AAA AGA GCA ACA CTG CAG CTA GTT GAT        1617
Glu Arg Met Arg Asp Glu Ser Lys Arg Ala Thr Leu Gln Leu Val Asp
                470                 475                 480

ATG GAG TGT GGC TAT CTG ACT GTT GAT TTC TTT CGG AAG CTT CCT CAA        1665
Met Glu Cys Gly Tyr Leu Thr Val Asp Phe Phe Arg Lys Leu Pro Gln
            485                 490                 495

GAT GTT GAT AAG GGT GGC AAT CCC ACA CAT TCA ATT TGT GAT AGA TAT        1713
Asp Val Asp Lys Gly Gly Asn Pro Thr His Ser Ile Cys Asp Arg Tyr
        500                 505                 510

AAT GAT TCA TAT CTA AGG CGA ATT GGA ACC ACA ATT TTG TCA TAT GTC        1761
Asn Asp Ser Tyr Leu Arg Arg Ile Gly Thr Thr Ile Leu Ser Tyr Val
    515                 520                 525

AAT ATG GTC TGT GCT ACT CTG CGG CAT TCA ATT CCC AAG TCC ATC GTC        1809
Asn Met Val Cys Ala Thr Leu Arg His Ser Ile Pro Lys Ser Ile Val
530                 535                 540                 545

TAT TGT CAA GTG CGG GAG GCA AAA CGA AGT CTA CTT GAT CAC TTT TTT        1857
Tyr Cys Gln Val Arg Glu Ala Lys Arg Ser Leu Leu Asp His Phe Phe
                550                 555                 560

ACC GAG CTA GGC AAA ATG GAG ATC AAG CGT CTG TCC TCG TTA CTG AAT        1905
Thr Glu Leu Gly Lys Met Glu Ile Lys Arg Leu Ser Ser Leu Leu Asn
            565                 570                 575

GAG GAT CCT GCA ATT ATG GAA CGA CGT AGT GCG CTC GCA AAG AGA CTA        1953
Glu Asp Pro Ala Ile Met Glu Arg Arg Ser Ala Leu Ala Lys Arg Leu
        580                 585                 590

GAG TTA TAC CGG AGT GCA CAA GCT GAA ATA GAT GCA GTT GCT TGG TCT        2001
Glu Leu Tyr Arg Ser Ala Gln Ala Glu Ile Asp Ala Val Ala Trp Ser
    595                 600                 605

AAG TAGAGATATG TATGTCAAAT CACGTTTATA CGAGAGCCAG CAGTGTCATT            2054
Lys
610

ATCATTGTTC ACTATTTTCT TATTCATACT CATTTTTCAT TGTCATCTTA TTCTGTTGCA     2114

TTTCCTCTTG AATAGATGAG ACGATTCTGA AAAAGGGAAA AAATGATTTT TTGGGTTATA     2174

TATAATTGAG TGTCCCTATA TCTTTCATTT TTCAGTC                              2211

(2) INFORMATION FOR SEQ ID NO:6:

(i) SEQUENCE CHARACTERISTICS:
        (A) LENGTH: 610 amino acids
        (B) TYPE: amino acid
        (D) TOPOLOGY: linear (ii) MOLECULE TYPE: protein (xi) SEQUENCE DESCRIPTION: SEQ ID NO:6:

Met Glu Asn Leu Ile Ser Leu Val Asn Lys Ile Gln Arg Ala Cys Thr
1               5                   10                  15

Ala Leu Gly Asp His Gly Glu Asn Ser Ala Leu Pro Thr Leu Trp Asp
            20                  25                  30

Ser Leu Pro Ala Ile Ala Val Val Gly Gly Gln Ser Ser Gly Lys Ser
        35                  40                  45

Ser Val Leu Glu Ser Val Val Gly Lys Asp Phe Leu Pro Arg Gly Ser
    50                  55                  60

Gly Ile Val Thr Arg Arg Pro Leu Val Leu Gln Leu His Lys Ile Asp
65                  70                  75                  80

Glu Gly Ser Arg Glu Tyr Ala Glu Phe Leu His Leu Pro Arg Lys Arg
                85                  90                  95

Phe Thr Asp Phe Val Ala Val Arg Lys Glu Ile Gln Asp Glu Thr Asp
            100                 105                 110

Arg Glu Thr Gly Arg Thr Lys Gln Ile Ser Ser Val Pro Ile His Leu
```

```
            115                 120                 125
Ser Ile Tyr Ser Pro Asn Val Val Asn Leu Thr Leu Ile Asp Leu Pro
    130                 135                 140

Gly Leu Thr Lys Val Ala Val Glu Gly Gln Pro Asp Ser Ile Val Lys
145                 150                 155                 160

Asp Ile Glu Asp Met Val Arg Ser Tyr Ile Glu Lys Pro Asn Cys Ile
                165                 170                 175

Ile Leu Ala Ile Ser Pro Ala Asn Gln Asp Leu Ala Thr Ser Asp Ala
                180                 185                 190

Ile Lys Ile Ser Arg Glu Val Asp Pro Thr Gly Asp Arg Thr Ile Gly
            195                 200                 205

Val Leu Thr Lys Ile Asp Leu Met Asp Lys Gly Thr Asp Ala Val Asp
210                 215                 220

Ile Leu Glu Gly Arg Ala Tyr Arg Leu Lys Phe Pro Trp Ile Gly Val
225                 230                 235                 240

Val Asn Arg Ser Gln Gln Asp Ile Asn Lys Asn Val Asp Met Ile Ala
                245                 250                 255

Ala Arg Arg Arg Glu Arg Glu Tyr Phe Asn Ser Thr Pro Glu Tyr Lys
                260                 265                 270

His Leu Ala Asn Arg Met Gly Ser Glu His Leu Ala Lys Met Leu Ser
            275                 280                 285

Lys His Leu Glu Thr Val Ile Lys Ser Lys Ile Pro Gly Ile Gln Ser
290                 295                 300

Leu Ile Asn Lys Thr Ile Ala Glu Leu Glu Ala Glu Leu Thr Arg Leu
305                 310                 315                 320

Gly Lys Pro Val Ala Ala Asp Ala Gly Gly Lys Leu Tyr Ala Ile Met
                325                 330                 335

Glu Ile Cys Arg Ser Phe Asp Gln Ile Phe Lys Asp His Leu Asp Gly
                340                 345                 350

Val Arg Pro Gly Gly Asp Lys Ile Tyr Asn Val Phe Asp Asn Gln Leu
            355                 360                 365

Pro Ala Ala Leu Lys Arg Leu Gln Phe Asp Lys Gln Leu Ser Met Glu
370                 375                 380

Asn Ile Arg Lys Leu Ile Thr Glu Ala Asp Gly Tyr Gln Pro His Leu
385                 390                 395                 400

Ile Ala Pro Glu Gln Gly Tyr Arg Arg Leu Ile Glu Ser Ser Leu Ile
                405                 410                 415

Thr Ile Arg Gly Pro Ala Glu Ser Ala Val Asp Ala Val His Ser Leu
            420                 425                 430

Leu Lys Asp Leu Val His Lys Ala Met Ser Glu Thr Leu Asp Leu Lys
        435                 440                 445

Gln Tyr Pro Gly Leu Arg Val Glu Val Gly Ala Ala Ser Val Asp Ser
    450                 455                 460

Leu Glu Arg Met Arg Asp Glu Ser Lys Arg Ala Thr Leu Gln Leu Val
465                 470                 475                 480

Asp Met Glu Cys Gly Tyr Leu Thr Val Asp Phe Phe Arg Lys Leu Pro
                485                 490                 495

Gln Asp Val Asp Lys Gly Gly Asn Pro Thr His Ser Ile Cys Asp Arg
            500                 505                 510

Tyr Asn Asp Ser Tyr Leu Arg Arg Ile Gly Thr Thr Ile Leu Ser Tyr
        515                 520                 525

Val Asn Met Val Cys Ala Thr Leu Arg His Ser Ile Pro Lys Ser Ile
530                 535                 540
```

-continued

```
Val Tyr Cys Gln Val Arg Glu Ala Lys Arg Ser Leu Leu Asp His Phe
545             550                 555                 560

Phe Thr Glu Leu Gly Lys Met Glu Ile Lys Arg Leu Ser Ser Leu Leu
                565                 570             575

Asn Glu Asp Pro Ala Ile Met Glu Arg Arg Ser Ala Leu Ala Lys Arg
            580                 585             590

Leu Glu Leu Tyr Arg Ser Ala Gln Ala Glu Ile Asp Ala Val Ala Trp
        595             600                 605

Ser Lys
    610
```

PHRAGMOPLASTIN AND METHODS OF EXAMINING CELL PLATE DEVELOPMENT

BACKGROUND OF THE INVENTION

The cell plate is a disc-like structure that is present only in dividing plant cells. Since cell plates are found only in plant cells, it is hoped that herbicides which directly and specifically block or interfere with cell plate development will be specific to plants and less hazardous to animals that may be exposed to such herbicides. Unfortunately, identifying such herbicides is hampered by a scarcity of tools and methods for rapidly and easily monitoring the effect of such herbicides on cell plate development.

Currently cell plate development is examined using phase contrast microscopy. However, some of the early stages of cell plate formation are difficult to examine using this tool. Cell plate development is also monitored by microscopic techniques in which the cells are first fixed and then incubated with aniline blue to stain the callose polysaccharide, which is a component of the cell wall. However, because callose is not deposited on the cell plate until the later stages of cell plate development, this technique also is not useful to monitor the early stages of cell plate formation and development.

Thus, it would be desirable to have additional tools and methods for examining the early stages of cell plate formation particularly in determining the effect of herbicides on cell plate development. Tools that do not require fixation or staining or other lengthy steps would also be desirable.

SUMMARY OF THE INVENTION

The present invention provides new tools and methods for identifying herbicides and potential herbicides which affect cell plate formation and development. A new protein, phragmoplastin, has been discovered which is associated with cell plate membrane vesicles during cytokinesis. By visualizing the phragmoplastin, one is able to examine the development of the cell plate particularly in response to herbicides or potential herbicides. One method of visualizing phragmoplastin employs immunocytochemical techniques with anti-phragmoplastin antibodies. Another method of visualizing phragmoplastin employs cells which are transformed with a DNA molecule which encodes a chimeric phragmoplastin protein comprised of phragmoplastin and a luminescent tag or protein, fused to the phragmoplastin protein. The phragmoplastin in such cells is visualized by examining the cells under conditions which cause the marker to become visible such as by fluorescent microscopy.

The present invention also relates to isolated DNA molecules which encode phragmoplastin, and cells transformed with DNA which encodes phragmoplastin, particularly DNA which encodes chimeric phragmoplastin proteins.

DESCRIPTION OF THE FIGURES

FIG. 1 is a nucleotide sequence, Seq. ID No. 3, of the phragmoplastin-encoding cDNA of plasmid pPDL5;

FIG. 2 is a nucleotide sequence, Seq. ID. No. 5, of the phragmoplastin-encoding cDNA of plasmid pPDL12;

FIG. 3 is the predicted amino acid sequence, Seq. ID No. 4, of the phragmoplastin encoded by the cDNA of plasmid pPDL5 as shown in FIG. 1;

FIG. 4 is the predicted amino acid sequence, Seq. ID No. 6, of the phragmoplastin encoded by the cDNA of plasmid pPDL12 as shown in FIG. 2;

DETAILED DESCRIPTION OF THE INVENTION

Figure 5:
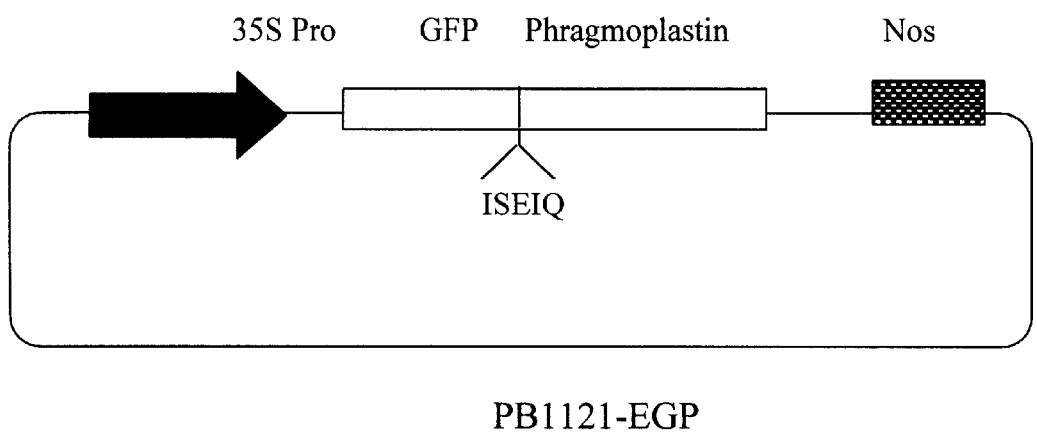
FIG. 5 is a map of plasmid pBI121 -EGP.

In accordance with the present invention, a new protein, phragmoplastin, which is spatially and temporally associated with the cell plate membrane during all stages of cell plate development has been discovered. By visualizing the phragmoplastin, one is able to examine the development of the cell plate particularly in response to herbicides or potential herbicides. The present invention relates to different methods of examining the effect of potential herbicides on cell plate development. In one embodiment, growing plant cells are treated with the herbicide. Then immunocytochemical methods which employ anti-phragmoplastin antibodies are used to visualize the distribution of the phragmoplastin within the cell and to determine whether the herbicide inhibits formation or development of the cell plate. In a second embodiment, the herbicide is administered to living transgenic plant cells comprising a DNA molecule which encodes the chimeric phragmoplastin protein. The effect of the herbicide on cell plate formation and development is determined by microscopy to visualize the distribution of the chimeric protein in transgenic cells that have been treated with the herbicide.

Phragmoplastin

On the basis of the predicted amino acid sequences depicted in FIGS. 3 and 4 and SEQ.ID NOS. 4 and 6, respectively, phragmoplastin has a calculated molecular weight of about 68.3 kDa. The phragmoplastin proteins depicted in SEQ.ID. NOS. 4 and 6 have three consensus sequences which are known to be involved in GTP binding: the G1 region $G(X)_4GK(ST)$ at position 41–48, the G3 region $DX_2G$ at position 142–145; and the G4 region (TN)(KQ)XD at position 211–214. All three GTP binding sequences are in the N-terminus region of phragmoplastin. The N-terminus of the phragmoplastin also comprises a self-assembly motif, which includes amino acid residues 49–93 of the phragmoplastin proteins depicted in SEQ. ID. NOS. 4 and 6. The phragmoplastin proteins also have a putative calcium/calmodulin-dependent protein kinase and cAMP-dependent protein kinase A site in the C-terminus, which is located at position 574 of the phragmoplastin proteins depicted in SEQ.ID.NOS. 4 and 6. Phragmoplastin has a 41.6% homology with the animal protein dynamin. Phragmoplastin, however, lacks the C-terminal proline-rich domain of dynamin. Phragmoplastin also lacks a transmembrane binding domain as found in dynamin.

The term "phragmoplastin" as used herein includes proteins which comprise the amino acid sequence of FIG. 3 and SEQ. ID. NO 4 and the amino acid sequence of FIG. 4 and SEQ. ID. NO.6. Phragmoplastin also includes proteins which have conservative amino acid substitutions in the sequences of SEQ.ID.NOS 4 and 6, proteins which are allelic variants of proteins comprising the amino acid sequences of SEQ. ID. NOS. 4 and 6, and proteins comprising amino acid sequences that are 80% homologous, preferably 90% homologous, more preferably 95% homologous to the sequences of SEQ. ID. NO 4 or SEQ.ID. NO. 6.

It has been discovered that phragmoplastin is localized in the perinuclear region of meristemic plant cells and is not concentrated in any specific areas during the early stages of the cell cycle. During early anaphase, when cell plate formation begins, phragmoplastin redistributes to the equator of the cell, where it is present across the entire cell plate disc within the phragmoplast cylinder. As the cell plate grows out toward the parental cell wall, phragmoplastin redistributes to the growing edge of the cell plate. On the basis of the structure of phragmoplastin and the redistribution of phragmoplastin to various areas of the cell during cytokinesis, it is believed that phragmoplastin plays a role in cell plate development and cell wall formation.

Because of the spatial and temporal association between phragmoplastin and the cell plate, phragmoplastin is a useful marker for cell plate formation and development in growing plant cells. Accordingly, antibodies to phragmoplastin are useful reagents for monitoring the effect of herbicides on cell wall formation and cell wall development. In addition, transformed cells that comprise a DNA molecule which encodes a chimeric protein comprising the phragmoplastin protein fused to a luminescent peptide or protein tag are also useful for monitoring the effect of herbicides on cell plate development in living cells. Such cell lines are particularly useful for screening for herbicides that bind to phragmoplastin or that specifically block redistribution of phragmoplastin in the cell.

Preparation of Phragmoplastin and Phragmoplastin Antibodies

Preferably, phragmoplastin is prepared using standard recombinant DNA methodology. Such methodology typically involves introducing a polynucleotide, preferably a DNA molecule, which encodes the phragmoplastin protein into a host cell. Following introduction of the polynucleotide into the host cell, the phragmoplastin encoding sequences is expressed in the host cell such that phragmoplastin protein molecules are formed in the cell.

Preferably, the introduced polynucleotide also comprises a promoter, more preferably an inducible promoter, operably linked to the phragmoplastin encoding sequence. Preferably, the polynucleotide further comprises a sequence which encodes a tag to facilitate isolation of the phragmoplastin protein such as, for example, an affinity tag and/or an epitope tag. Preferably, the tag sequences are at the 5' or 3' end of the phragmoplastin-encoding sequence. The polynucleotide preferably also comprises nucleotide sequences that encode a replication origin and a selectable marker.

The polynucleotide comprising the phragmoplastin-encoding sequence is introduced into the host cell by conventional methods, such as, by cloning the polynucleotide into a vector and by introducing the vector into the host cell by conventional methods. Suitable host cells include, for example, bacterial cells, yeast cells, mammalian cells, and plant cells. The DNA sequences of the introduced polynucleotide are then expressed in the host cell. Thereafter the expressed protein is isolated from the host cell using conventional methods such as for example, chromatography and gel electrophoresis.

Although less preferred, phragmoplastin can also be prepared using conventional synthetic biochemical techniques, such as solid phase peptide synthesis.

In a preferred method, phragmoplastin and anti-phragmoplastin antibodies were prepared using the following procedures.

Cloning cDNA Molecules which Encode Phragmoplastin Protein from Dividing Plant Cells cDNA clones which encode phragmoplastin were obtained using the following primers:

5'-CCI(AC)G(AC)GG(AT)(AT)(GC)TGGIAT(TC)G-TIAC-3', SEQ.ID.NO. 1 and 5'-TTT(TG)GTIA(AT)(AG) ACICC(ATG)ATIGT-3', SEQ.ID. NO.2.

and soybean nodule poly(A) RNA, that had been isolated from 15-day-old root nodules using oligo (dT). The isolated poly(A)RNA was then reverse transcribed into cDNA using oligo(dT). PCR amplification of the resulting product was performed as 45 cycles at 94° C. for 40 seconds; 55° C. for 40 seconds; and 72° C. for 1 minutes The resulting 500 base pair fragment obtained was blunt-end ligated into the SmaI site of pUC19 and used as a probe to screen a λ-ZapII soybean nodule cDNA library. Four positive clones were identified after screening $1 \times 10^6$ plaques. The positive clones were excised and ligated into plasmids obtained from Stratagene and sequenced using the procedure of Sanger et al, 1977, in Proc. Nat. Acad Sci. USA 74:5463–5467. Sequence analysis indicated that three of these clones, including the longest clone pPDL5, are encoded by the same gene. The other clone, pPDL12, is encoded by a different gene. The nucleotide sequence of the pPDL5 clone is shown in FIG. 1 and SEQ. ID. NO. 3. The nucleotide sequence of the pPDL12 clone is shown in FIG. 2 and SEQ. ID. NO. 5.

As shown in FIGS. 1 and 2, both pPDL5 and pPDL12 contain nearly full-length cDNA inserts with poly(A) tails and with 5' non-coding regions of 126 base pairs (pPDL5) and 159 base pair (pPDL 12). Each of these two nucleotide sequences contains a long open reading frame of 1930 base pairs corresponding to a protein of 610 amino acids in length with a calculated molecular weight of 68.3 kDa. The two clones differ in the N-terminal and C-terminal non-coding regions, but share 98% homology in their coding-regions.

Polynucleotide molecules which encode phragmoplastin protein include, for example, the nucleotide sequences of SEQ. ID. NO. 3 or SEQ.ID.NO.5 or nucleotide sequences which hybridize under stringent conditions to the sequences of SEQ.ID. NOS. 3 or 5. As used herein, the term "stringent conditions" means hybridization will occur if there is at least 90% identity between the polynucleotide sequence and one of SEQ.ID. NO. 3 or 5. Thus, the polynucleotide molecules which encode phragmoplastin include, for example, DNA, which DNA includes cDNA, genomic DNA, and synthetic DNA, and RNA sequences encoding allelic variant forms of the peptides encoded by the cDNA of SEQ. ID. NOS. 3 and 5. Preferably the DNA or RNA is provided in a purified or isolated form. The polynucleotide molecules which encode phragmoplastin optionally encode a marker sequence which allows for purification of the phragmoplastin, such as for example an affinity tag or epitope tag. The polynucleotide molecules which encode phragmoplastin optionally encode a sequence which encodes a luminescent peptide or protein fused to the coding sequence for phragmoplastin.

Purification of Phragmoplastin from E.coli Transformed with a cDNA Molecule that Encodes Phragmoplastin The BgIII-KpnI fragment of pPDL12 was cloned in frame into the BamHI-KpnI site of bacterial expression vector pRSETC, which had been obtained from Invitrogen.

The resulting construct pEPDL-12 contains an isopropyl-B-D-thiogalactopyranoside (IPTG)-regulatable promoter operably linked to a coding sequence for a polyhistidine metal binding domain fused to the coding sequence of the phragmoplastin protein. The construct was then transformed into E.coli Lys-s cells. The cells were grown in Luria-Bertani (LB) medium to identify transformants. Expression of the phragmoplastin protein was induced by adding 0.5 mM IPTG to the medium of the transformed cells. Phragmoplastin protein was purified from a solubilized cell pellet by chromatography on a Nickel(Ni) chelate column obtained from Invitrogen. The Ni- affinity chromatography was conducted under non-denaturing conditions according to the manufacturer's instructions. The protein eluted from the Ni column was further purified by sodium dodecyl sulfate polyacrylamide gel electrophoresis (SDS-PAGE). The gel-purified phragmoplastin protein was cut out from the polyacrylamide gel and ground in liquid nitrogen to provide the gel-purified phragmoplastin.

A single band of protein with an apparent molecular weight of 72 kDa was obtained after Ni-affinity chromatography. The molecular weight of the expressed protein results from fusion of a 35 amino acid polyhistidine metal binding domain and a four amino acid linker sequence to the N-terminus of the expressed phragmoplastin protein molecules. The expressed protein also has the ability to hydrolyze GTP without the requirement for any other protein factors. Thus, phragmoplastin has intrinsic GTPase activity.

Preparation of Antibody to Phragmoplastin

To prepare antibodies, the gel-purified phragmoplastin was directly injected into rabbits using conventional techniques. The animals were bled and the serum subjected to protein A gel chromatography as described in Harlow and Lan, "Antibodies," A Laboratory Manual. Cold Spring Harbor Laboratory, 1988 to provide anti-phragmoplastin antibodies.

Assaying for Phragmoplastin at Different Stages of the Cell Cycle

The anti-soybean antiphragmoplastin antibodies prepared as described above were used to assay for phragmoplastin in tobacco BY-2 cells synchronized at S phase, metaphase, and cytokinesis by the methods of Asada and Shibaoka as described in J. Cell Sci., 107: 2249–2257, 1994, and in cells obtained from soybean root tips. A band with a molecular mass of about 68 kDa was detected with the anti-soybean phragmoplastin antibody in the lanes containing proteins extracted from both dividing soybean root cells and dividing tobacco BY-2 cells, indicating that phragmoplastin is conserved in plants. Thus, anti-soybean phragmoplastin antibodies are able to bind to phragmoplastin from various species of plants. Phragmoplastin in tobacco cells and soybean was most abundant in the microsomal membrane fractions with a very low concentration in the cytosolic fractions. The ratio of phragmoplastin in microsomes and in the cytosol did not change during the cell cycle, indicating that phragmoplastin is associated primarily with membranes at all stages of the cell cycle.

Methods for Examining Cell Plate Development

Because phragmoplastin is spatially and temporally associated with the cell plates in dividing cells, polyclonal and monoclonal anti-phragmoplastin antibodies enable one to monitor the distribution of phragmoplastin in dividing plant cells and to examine cell plate development. Preferably, the antibodies are used in an immunolabeling method. The antibodies are used to immunolabel dividing cells, such as for examples cells that have been obtained from root tips or plant cell cultures. During the immunolabeling procedure, the cells are fixed, permeablized and incubated with the anti-phragmoplastin antibody. Optionally, the cell walls are removed prior to incubation with the anti-phragmoplastin antibody to improve labeling. Then, the cells are incubated with a second antibody which binds to the anti-phragmoplastin antibody and which carries a fluorescent or chemiluminescent tag. The cells are then visualized under a microscope and the distribution of the immunolabeled phragmoplastin in the cell determined.

The following examples of methods which use phragmoplastin antibodies to examine cell plate formation and development in dividing cells are illustrative and are not meant to limit the scope of the invention.

EXAMPLE 1

Immunolabeling Cell Plates in Dividing Cells

Four-day-old soybean root tips or eleven-day-old nodules were fixed in 4% paraformaldehyde in buffer containing 60 mM PIPES, 25 mM HEPES, 10 mM EGTA, 2 mM $MgCl_2$, pH 7.0 (PHEM buffer) for 2 hours at room temperature and then washed with washing buffer containing 10 mM MES, pH 5.7, 30 mM $CaCl_2$, 0.1% BSA, 5 mM 2-mercaptoethanol, 0.4 M mannitol for 30 minutes. The plant tissues were then digested in a solution containing 2% cellulase from Calbiochem, 1% macerozyme R-10 from Ykult, Honsha, Japan, 0.5% pectolyase Y23 from Karlan in washing buffer for 15 minutes. After rinsing in PHEM buffer, the plant tissues were squashed between coverslips to release the individual cells. The cells were air dried for 10 minutes and then permeablized with 0.5% Triton X-100 in PHEM for 5 minutes. The phragmoplastin in the cells was then immunolabeled using affinity-purified anti-phragmoplastin IgG as the first antibody and fluorescein isothiocyanate (FITC)-conjugated anti-rabbit goat IgG as a second antibody. Pre-immune serum was used as the first antibody in the control group. DNA was stained with 4'6'-diamidino-2-phenylindole (DAPI) at a concentration of 10 μg/ml for 5 minutes at room temperature. Cells were visualized in a confocal or fluorescent microscope equipped with excitation/emission filter sets for FITC. Photographs of the intact cells were taken in phase contrast, and using appropriate filters for FITC and DAPI stainings.

In metaphase when the two sets of chromosomes just begin to separate, no cell plate could be visualized by anti-phragmoplastin antibody labeling or phase contrast microscopy. However, by late anaphase or early telophase, the inter-zone region of the dividing plant cell could be visualized with anti-phragmoplastin antibodies. In comparison, phase contrast microscopy did not enable visualization of the cell plate in anaphase. When the cells reached telophase, the cell plate could be distinguished in the phase contrast image. During telophase the anti-phragmoplastin antibody first reacted with the entire width of the cell plate and then with the periphery of the cell plate. When the two daughter cells separated completely, the anti-phragmoplastin antibody gave a perinuclear particulate staining pattern. No phragmoplastin fluorescence was observed on the newly formed plasma membranes or cell walls of these two daughter cells.

The anti-phragmoplastin antibodies enabled the cell plate to be visualized from a point at the earliest stages of cell plate formation in early anaphase until the very latest stages of cell plate formation when the cell plate reaches the parental cell wall.

EXAMPLE 2

Immunolabeling the Cell Plate and Microtubules in Dividing Cells

Intact cells from soybean root tips were treated as described above in example 1 except that the permeabilized cells were also incubated with mouse anti-tubulin IgG, obtained from Amersham and with tetramethylrhodamine isothiocyantate (TRITC)-conjugated goat anti-mouse IgG from Sigma to stain the microtubules. The double-labeled cells were visualized in a confocal microscope equipped with dual excitation/emission filter sets for both FITC and TRITC. Photographs of the cells were taken in phase contrast, and using white light and blue light and appropriate filters for FITC, TRITC and DAPI fitted to a Zeiss microscope.

A metaphase spindle and phragmoplasts at different stages of cytokineses were clearly distinguished with microtubule labeling. The bright line of phragmoplastin fluorescence first appeared in cells at anaphase. As the cell plate grew outwards, both the phragmoplastin protein fluorescence and the microtubule fluorescence decreased in the middle of the phragmoplasts. However, a bright fluorescence line of phragmoplastin protein was still visible at the end of cytokinesis when microtubule fluroescence had almost disappeared. These results indicate that the distribution of phragmoplastin is related to but independent from microtuble formation during cytokinesis. Thus, anti-phragmoplastin antibodies allow one to visualize and characterize events in cell plate formation and development that cannot be examined using anti-tubulin antibodies.

EXAMPLE 3

Immunolabeling the Cell Plate and Microtubules in Dividing Cells

Three-day-old tobacco BY-2 cells were fixed in 4% paraformaldehyde in 60 mM Pipes, 25 mM Hepes, 10 mM EGTA, and 2 mM MgC12, pH 7.0 (PHEM) for I hours at room temperature and then washed on one layer of Miracloth with buffer containing 10 mM MES, pH 5.7, 30 mM $CaCl_2$, 0.1% BSA, 5 mM β-mercaptoethanol and 0.4 M mannitol. Cells were then digested for 15 minutes in a solution containing 1% cellulase from Calbiochem, San Diego, Cailf. and 0.1 % pectolyase Y23 in washing buffer. After rinsing with PHEM buffer, cells were transferred to poly-L-lysine-coated slides and air dried for 10 minutes. Immunofluorescence microscopy was then carried out using the affinity-purified anti-soybean phragmoplastin IgG as the first antibody and the fluorescein isothiocyanate (FITC)-conjugated anti-rabbit goat IgG as a second antibody. Preimmune serum was used as the first antibody in the control group. For double-labeling experiments, mouse anti-tubulin IgG from Amersham and tetramethylrhodamine isothiocyanate (TRITC)-conjugated goat anti-mouse IgG from Sigma were used to stain microtubules. DNA was stained with DAPI at a concentration of 10 µg/ml for 5 minutes at room temperature and microscopy conducted as described above in example 2.

Immunofluorescence microscopy using anti-soybean phragmoplastin antibodies demonstrated that phragmoplastin is associated with cell plates in tobacco BY-2 cells. In the early stages of cell plate formation, phragmoplastin was present across the entire cell plate disc within the phragmoplast proper. As the cell plate grew outward, phragmoplastin was concentrated more on the growing margins of the cell plate whereas the concentration in the middle of the cell plate decreased. A ring-like, annular distribution pattern of phragmoplastin fluorescence was observed at this stage in many cells. As cell plate formation was completed, phragmoplastin disappeared, and only a perinuclear diffused pattern of phragmoplastin was visible in the nondividing cells. Thus, antibodies to phragmoplastin enable the cell plates to be marked and to differentiate the early and late stages of cell plate formation and development.

Preparation of a Transgenic Cell Line

Transgenic cells which express a chimeric phragmoplastin protein that can be visualized in living cells by microscopy are prepared by transforming plant cells with a vector, such as for example the plant vector Agrobacterium which contains a DNA molecule that encodes phragmoplastin linked at its N-terminus or C-terminus to a luminescent polypeptide. In a preferred embodiment, cultured plant cells with a vector containing a DNA molecule having a coding sequence for phragmoplastin protein linked to a coding sequence for the green fluorescence protein (GFP) as described below to provide transgenic cell lines that express the chimeric phragmoplastin protein, GFP-phragmoplastin.

The plasmid pBI-35S-mGFP, which contains a nucleotide sequence encoding the GFP was obtained from J. Haesoloff, MRC Laboratory, Cambridge, UK. A plasmid containing the GFP encoding sequence can also be obtained from Clonetech Labs, Palo Alto, Calif. The plasmid was amplified using standard techniques and then the GFP coding region was cloned into plasmid pUC-GFP44 obtained from Dr. Z. Yang, Ohio State University, Columbus, Ohio. The GFP coding region was then excised and ligated into the XbaI-SacI sites of PBI221-JR, also obtained from Dr. Z. Yang, to provide plasmid pE-GFP44, which contained a Cauliflower mosaic virus 35S promoter, a GFP coding sequence with a BglII site at the C-terminal end, and a nopaline synthase terminator. The BglII-SacI fragment of phragmoplastin coding sequence as shown in SEQ. ID. NO. 5 was removed from plasmid pEPDL12, prepared as described above, and cloned into the BglII-SacI sites of pE-GFP44 to provide the plasmid pE-GFP44-PDL-BS. The XbaI-SacI fragment of the plasmid pE-GFP44-PDL-BS was finally cloned in to XbaI-SacI sites of plasmid pBI121-MLB-PDL12, obtained from Clonetech Labs, Palo Alto, Calif. to provide plasmid pBI121-EGP, which is depicted in FIG. 5. Plasmid pBI121-EGP contained a 35S promoter, a coding sequence for a GFP-phragmoplastin, and a nopaline synthase terminator. Plasmid pBI 121 -EGP was transformed into *Agrobacterium tumefaciens* LBA4404 using a freeze-thaw method.

Transformation of BY-2 cells was performed using the procedure of An et al., "Binary Vectors", In Plant Molecular Biology Manual, pp A3/1, 1992. A five ml liquid culture of 3-day-old BY-2 cells was mixed with 100 µL of *Agrobacterium tumefaciens* LBA4404 harboring the plasmid pBI121-EGP. The cells were allowed to grow in Petri plates at 25° C. without shaking for 2 days. Cells were then filtered on one layer of Miracloth and washed to remove most of the bacteria. The washed cells were then plated on solid Murashige and Skoog medium containing 300 µg kanamycin and 500 µg of carbenicillin. Transgenic calli usually emerged after 2–3 weeks. The calli were then transferred to new antibiotic-containing plates.

Transgenic cells (20 mg fresh weight) from different calli were digested for 20 minutes at room temperature in 200 µL of enzyme solution of 1% cellulase in 10 mM Mes, pH 5.7 and 0.38 M sorbitol. Cells were then centrifuged for 2 minutes in a microcentrifuge at room temperature. The enzyme solution was removed and the cells were washed with 200 µL of washing solution containing 1% Triton X-100 in PHEM. After pelleting, the cells were directly solubilized in SDS sample buffer and processed for SDS-PAGE and protein gel blotting. All transgenic lines except one were found to express GFP-phragmoplastin, which has a molecular weight of approximately 90 kDa as determined by SDS-gel electrophoresis. About 50% of the kanamycin-resistant cell lines tested were found to express GFP-phragmoplastin at a level 2 to 5 fold higher than native phragmoplastin protein and three lines overexpressed the GFP-phragmoplastin at levels that were 5 to 10 fold higher than the levels of native phragmoplastin in untransformed BY-2 cells.

GFP-phragmoplastin is stable in the transgenic BY-2 cells. Even though a degradation product of the native phragmoplastin was found in most of the preparations, no degradation products of GFP-phragmoplastin were detected by protein gel blots analysis. The degradation products of the native phragmoplastin were not detected if cell extract was made in the presence of proteinase inhibitors. Similar to the native phragmoplastin, the GFP-phragmoplastin was predominantly associated with the microsomal membrane fraction.

Fluorescence microscopy showed that the transgenic cells overexpressing GFP-phragmoplastin at 2 to 10 fold higher than native phragmoplastin exhibited bright green fluorescence on the cell plate during cytokinesis, whereas no green fluorescence was observed in untransformed BY-2 cells. Control BY-2 cells, which were transformed with GFP alone exhibited a green fluorescence throughout the cytoplasm but did not exhibit a defined fluorescent line in the cell plate region. Thus, the targeting of the GFP-phragmoplastin to the cell plate is the function of the phragmoplastin part of the chimeric protein.

The development of the cell plate was examined in transgenic cells which were prepared as described above and which overexpress GFP-phragmoplastin to levels 5 to 10× greater than the levels of native phragmoplastin in untransformed BY-2 cells. All transgenic cells were grown on solid medium or in liquid medium. Then 100 $\mu$L of liquid culture cells were mixed with 100 $\mu$L of medium in a culture well on a slide. The development of the cell plate in the cells was examined over time in an individual cell by visualizing the GFP-phragmoplastin fluorescence under an inverted epifluoresence microscope equipped with an FITC filter set and taking photographs of the cell at different stages in the cell cycle. To reduce photobleaching, an excitation light was turned on only when photographs were taken.

In the early stages of cell plate formation, the GFP-phragmoplastin appeared as a dense short fluorescent line in the center of the dividing cells. The GFP-phragmoplastin fluorescence appeared soon after the onset of anaphase and gradually increased in intensity forming a short line within 30 minutes. As the cell plate expanded outward, the fluorescence in the center of the cell plate decreased while the intensity of the fluorescence at the margin of the cell plate increased. Thereafter, a ring-like, annular fluorescence was observed in the cell. As the cell plate enlarged, there was a gradual decrease of the overall intensity of the GFP-phragmoplastin fluorescent ring. After the cell plate reached the parental cell wall, the green fluorescence gradually disappeared. The fluorescence of GFP-phragmoplastin on the cell plate remained stable up to 2 hours. Thus, the chimeric protein GFP-phragmoplastin follows the same pattern of distribution during cytokinesis as native phragmoplastin.

During the initial stages of cell plate formation, the GFP-phragmoplastin fluorescence was confined to the center of the phragmoplast proper. During the later stage, when the cell plate extended beyond the phragmoplast proper, the GFP fluoroescence redistributed to the growing edge of the cell plate. Thus, GFP-phragmoplastin, like native phragmoplastin is associated with the cell plate.

In the cells which overexpressed GFP-phragmoplastin to levels that were more than 5 to 10 fold greater than native phragmoplastin, the time for the cell plate to fuse with the prenatal cell wall was greater than in non-transformed cells and often resulted in the formation of an oblique cell plate. The fact that these transgenic cells continued to elongate, irrespective of the orientation of cell division, indicates that in these particular cell lines the plane of cell division is uncoupled from the direction of cell elongation.

Transgenic cells which overexpress a phragmoplastin protein fused to a luminescent marker permit observation of cell plate development in a living cell continuously and throughout the entire process of cytokinesis. Accordingly, such transgenic cell lines provide a research tool which avoids many of the problems that are encountered when conventional research tools are used to examine cell plate formation. For example, use of the transgenic cell lines eliminates the need to fix the cells, which can occasionally distort subcellular structures. Use of the transgenic cell line also avoids the lengthy staining steps which are often required to examine cell plate development. Use of the transgenic cell line also permits examination of cell plate development in a single cell, and as such, avoids any problems that may result from observing a dynamic process in a multitude of cells which appear to be in different stages of the cell cycle. Thus, it is less likely that short-lived steps in cell plate development will be overlooked when such transgenic cell lines are used to examine cell plate development.

Examining the Effect of Herbicides on Cell Plate Development

In one embodiment, the effect of herbicides whether known herbicides or herbicides on cell plate development is examined using anti-phragmoplastin antibodies. Preferably, the antibodies are used in an immunolabeling method which commences with application of the herbicide to dividing plant cells. Preferably various concentrations of the herbicide are applied to determine the optimum concentration for inhibiting cell plate development. Although the herbicide may be applied to a whole plant or plant segment that comprises dividing cells, it is preferred that the herbicidal compound be added directly to the medium of plant cell cultures. The use of plant cell cultures eliminates the step of dissociating the cells of the growing plant. In addition, the use of plant cell cultures allows synchronization of the dividing cells to the same stages of mitosis. When applied to synchronized cells, it is preferred that the herbicidal compound be applied before anaphase. Thereafter, the cells typically are fixed, permeablized and incubated with the anti-phragmoplastin antibody. Optionally, the cell walls are removed prior to incubation with the anti-phragmoplastin antibody to enhance labeling with the antibody. Preferably, the cells are then incubated with a second antibody which binds to the anti-phragmoplastin antibody and which carries a fluorescent or chemiluminescent tag. The cells are then visualized under a microscope and the distribution of the immunolabeled phragmoplastin in the cell is determined to identify herbicides which inhibit cell plate formation and development and to characterize the stages in cell plate development where such herbicides exert their effect.

In a second embodiment, the herbicide is applied to transgenic plant cells that express a chimeric phragmoplastin protein that comprises phragmoplastin fused to a luminescent peptide or protein tag. Thereafter, the distribution of the chimeric protein within the living cell is continuously monitored to determine the effect of the herbicide on cell plate development. To permit easy visualization of the chimeric protein, it is preferred that the transgenic cells overexpress the chimeric protein to levels that are 5 to 10 fold higher than the level of native phragmoplastin. Preferably, the transgenic cells are synchronized prior to treatment with the herbicide. Preferably, the herbicide is applied to the cells at various stages in the cell cycle, including metaphase, anaphase, and telophase. Preferably, the distribution of the chimeric protein is monitored over time in living cells that have not been fixed or permeabilized. Preferably, the distribution of the chimeric protein is monitored using microscopy, such as for example, epifluorescence microscopy as described in examples 3 and 4 or wide-field microscopy followed by image deconvolution as described by Gens J. S. et al. in Protoplasma 194:215–230, 1996 which is incorporated herein by reference EXAMPLE 4
Effect of Caffeine on Cell Plate Development Caffeine inhibits cell plate development in plant cells. To determine whether caffeine affects the early stages or later stages of cell plate development in living cells, 100 μL of liquid culture transgenic BY-2 cells that were overexpressing GFP-phragmoplastin, prepared as described above, were mixed with 100 μL of medium in a culture well. One of the dividing transgenic cells was then located under an inverted epifluorescence microscope and the presence of the GFP-phragmoplastin fluorescence at the center of the cell and on the cell plate was recorded. Then 50 μL of caffeine was added to the medium in the culture chamber to a final concentration 10 mM. Thereafter the distribution of the GFP-phragmoplastin fluorescence in the cell was monitored and recorded by photographing the same cell at different time intervals following addition of the caffeine to the medium. Photographs were taken for 2 hours following addition of the caffeine.

EXAMPLE 5
Effect of Taxol on Cell Plate Development

The effect of taxol on cell plate development was determined as described in example 4 for caffeine, except that 10 μL of taxol rather than caffeine was added to the medium to a final concentration 50 mM.

As shown by the photographs of the transgenic cells of example 4, caffeine treatment had no apparent effect on the distribution of phragmoplastin on the cell plate during the early stages of cell plate development. However, at the later stages of cell plate development, caffeine treatment blocked the increase in phragmoplastin at the growing margins of the cell plate. Thereafter, the phragmoplastin fluorescence on the cell plate started to disappear from the periphery and accumulate in the center of the cell plate. This is in sharp contrast to the control transgenic cells in which the phragmoplastin fluorescence in the periphery increases while the phragmoplastin fluorescence in the center decreases as the cell plate extends to meet the prenatal cell wall.

As shown by the photographs of the transgenic cells of example 5, the re-distribution of phragmoplastin on the cell plate in the taxol-treated transgenic cells was very different from the re-distribution of phragmoplastin on the cell plate in control transgenic cells and caffeine-treated transgenic cells. Taxol immediately stopped the outward redistribution of phragmoplastin. The green ring of GFP-phragmoplastin fluorescence was present in the cells of example 5 throughout the 2 hour observation period. There was no change in shape or size of this ring. It is believed that that the effect of the taxol on cell plate development and phragmoplastin distribution in the Numerous modifications and variations of the present invention are possible in light of the above teachings and are, therefore, within the scope of the appended claims.

What is claimed is:

1. An isolated polynucleotide encoding a phragmoplastin protein having a molecular weight of about 65 to 70 kDa and at least one GTP binding domain, wherein said phragmoplastin protein has an amino acid sequence selected from the group consisting of the amino acid sequence of SEQ ID NO. 4 and the amino acid sequence of SEQ ID NO. 6.

2. The isolated polynucleotide of claim 1, wherein the isolated polynucleotide encodes a phragmoplastin protein comprising the amino acid sequence of SEQ ID NO. 4.

3. The isolated polynucleotide of claim 1, wherein the isolated polynucleotide encodes a phragmoplastin protein comprising the amino acid sequence of SEQ ID NO.6.

4. The isolated polynucleotide of claim 1 wherein the polynucleotide comprises a sequence selected from the group consisting of (a) the nucleotide sequence of the protein coding region of SEQ. ID. NO. 3;

(b) the nucleotide sequence of the protein coding region of SEQ. ID. NO.5: and (c) a sequence which is complementary to the nucleotide sequence of (a) or (b).

5. The isolated polynucleotide of claim 1 wherein the polynucleotide is DNA.

6. The isolated polynucleotide of claim 1 wherein the polynucleotide encodes a chimeric phragmoplastin protein which comprises a phragmoplastin protein fused to a luminescent peptide tag.

7. The isolated polynucleotide of claim 1 wherein the peptide tag is a fluorescent protein.

* * * * *